US 6,686,995 B2

(12) United States Patent
Wilk et al.

(10) Patent No.: US 6,686,995 B2
(45) Date of Patent: Feb. 3, 2004

(54) TWO-DIMENSIONAL UV COMPATIBLE PROGRAMMABLE SPATIAL FILTER

(75) Inventors: Dieter E. Wilk, San Jose, CA (US); Anlun Tang, Pleasanton, CA (US); Eric N. Vella, Mountain View, CA (US); Rex Runyon, Fremont, CA (US); Jamie Michael Sullivan, Sunnyvale, CA (US); Ralph Thomas Johnson, Los Gatos, CA (US)

(73) Assignee: KLA-Tencor Technologies Corporation, San Jose, CA (US)

( * ) Notice: Subject to any disclaimer, the term of this patent is extended or adjusted under 35 U.S.C. 154(b) by 0 days.

(21) Appl. No.: 10/163,762

(22) Filed: Jun. 4, 2002

(65) Prior Publication Data

US 2004/0001198 A1 Jan. 1, 2004

Related U.S. Application Data

(60) Provisional application No. 60/368,607, filed on Mar. 28, 2002.

(51) Int. Cl.[7] ............................................... G01N 21/88
(52) U.S. Cl. ............................... 356/237.3; 356/237.4; 356/237.5
(58) Field of Search ........................... 356/237.1, 237.2, 356/237.3, 237.4, 237.5, 71; 250/550

(56) References Cited

U.S. PATENT DOCUMENTS

| | | | | |
|---|---|---|---|---|
| 5,276,498 A | * | 1/1994 | Galbraith et al. | ......... 356/237.2 |
| 5,420,709 A | * | 5/1995 | Kato et al. | ..................... 349/25 |
| 5,463,491 A | * | 10/1995 | Check, III | .................. 359/296 |
| 5,691,795 A | | 11/1997 | Doane et al. | |
| 5,822,055 A | | 10/1998 | Tsai et al. | ..................... 356/237 |
| 6,201,601 B1 | | 3/2001 | Vaez-Iravani et al. | ... 356/237.4 |

OTHER PUBLICATIONS

P.Y. Lui, L.C. Chien, Assemble–Averaged Dynamic Light Scattering from Polymer–Stabilized Liquid Crystals, Mol. Cyrs. Liq. Cyrs. 348, 187–205 (2000).

* cited by examiner

*Primary Examiner*—Richard A. Rosenberger
*Assistant Examiner*—Vincent P. Barth
(74) *Attorney, Agent, or Firm*—Beyer, Weaver & Thomas, LLP.; Mary R. Olynick, Esq

(57) ABSTRACT

Disclosed are mechanisms for selectively filtering spatial portions of light emanating from a sample under inspection within an optical system. In one embodiment, a programmable spatial filter (PSF) is constructed from materials that are compatible with light in a portion of the UV wavelength range. In a specific implementation, the PSF is constructed from a UV compatible material, such as a polymer stabilized liquid crystal material. In a further aspect, the PSF also includes a pair of plates that are formed from a UV grade glass. The PSF may also include a relatively thin first and second ITO layer that results in a sheet resistance between about 100 and about 300 Ω per square. The PSF provides selective filtering in two directions. In other words, the PSF provides two dimensional filtering.

30 Claims, 5 Drawing Sheets

TWO-DIMENSIONAL UV COMPATIBLE PROGRAMMABLE SPATIAL FILTER

CROSS-REFERENCE TO RELATED APPLICATION

This application takes priority under U.S.C. 119(e) of United States Provisional Application No. 60/368,607 filed Mar. 28, 2002 entitled, "UV COMPATIBLE PROGRAMMABLE SPATIAL FILTER" by Dieter E. Wilk, Anlun Tang, Eric N. Vella and Rex Runyon which is incorporated by reference in its entirety for all purposes.

BACKGROUND OF THE INVENTION

The present invention relates generally to optical inspection systems for detecting defects on a sample. More specifically, it relates to mechanisms for filtering noise from the detection of defects within such optical systems.

Many instruments currently available for detecting small particles on wafers, reticles, photo masks, flat panels and other specimens use darkfield imaging. Under dark field imaging, flat, specular areas scatter very little signal back at the detector, resulting in a dark image, hence the term dark field. Surface features and objects that protrude above the surface scatter more light back to the detector. In darkfield imaging, the image is normally dark except areas where particles or circuit features exist. A darkfield particle detection system can be built based on the assumption that particles scatter light more than circuit features.

In darkfield type optical inspection systems, an intense light beam in the visible wavelength range is directed towards a sample. Light scattered from the sample in response to such incident beam is then collected by a detector. The detector generates an image of the sample from the scattered light. Since defects, such as particles or voids, cause the incident light to scatter, scattered light may indicate the presence of such a defect. However, other features of the sample that are not defects may cause the incident beam to scatter resulting in the detection of "false" or "nuisance" defects. For example, repeating patterns on the sample, which are typically present on a semiconductor device, cause incident light to scatter so that sharp bright spots are imaged on the detector. These sharp bright spots may obscure actual defects. Additionally, line features at specific angles on a sample may result in scattering in broad regions of the image at specific angles, e.g., 45° and 90°, which also obscures detection of "real defects."

There are instruments that address some aspects of the "nuisance defect" problems associated with darkfield. One method in use today to enhance the detection of particles is spatial filtering. Under plane wave illumination, the intensity distribution at the back focal plane of a lens is proportional to the Fourier transform of the object. Further, for a repeating pattern, the Fourier transform consists of an array of light dots. By placing a filter in the back focal plane of the lens which blocks out the repeating light dots, the repeating circuit pattern can be filtered out and leave only non-repeating signals from particles and other defects under certain ideal conditions.

Although conventional Liquid Crystal type spatial filters work well within inspection systems that operate in the visible light range, they fail to effectively inhibit light in the ultraviolet (UV) region from nuisance sources from reaching the detectors. A UV light source may be used for any number of reasons, e.g., to effectively detect smaller sized defects. However, a conventional spatial filter's extinction capability is greatly reduced when going from a visible to an UV light source. Additionally, a conventional spatial filter fails to effectively transmit scattered light in the UV region. In a specific example, a conventional PSF has an extinction value of 200:1 and a transmission value of 20 percent at the UV wavelength of 364 nm. It should be noted that the extinction ratios described herein are measured with a detector that is at a distance of 10 inches from the filter and has an aperture of 1 centimeter. Finally, both the transmission and extinction performance of conventional spatial filters degrade over time under UV light exposure.

Accordingly, there is a need for an improved liquid crystal type programmable spatial filter for use in a darkfield optical inspection system that has improved extinction and transmission performance in the UV region.

SUMMARY OF THE INVENTION

Accordingly, mechanisms are provided for selectively filtering spatial portions of light emanating from a sample under inspection within an optical system. In one embodiment, a programmable spatial filter (PSF) is constructed from materials that are compatible with light in a portion of the UV wavelength range. In a specific implementation, the PSF is constructed from a UV compatible material, such as a polymer stabilized liquid crystal material. In a further aspect, the PSF also includes a pair of plates that are formed from a UV grade glass. The PSF may also include a relatively thin first and second ITO layer that results in a sheet resistance between about 100 and about 300 Ω per square. The PSF provides selective filtering in two directions. In other words, the PSF provides two dimensional filtering.

In one embodiment, an optical inspection system for detecting anomalies on a sample is disclosed. The inspection system includes a light source for directing an incident light beam onto a sample and a programmable spatial filter (PSF) arranged in a path of light emanating from the sample in response to the incident light beam. The PSF is configurable to inhibit or transmit one or more selected portions of the emanating light, and the selected portions of the emanating light may be selected from a plurality of emanating light portions arranged along a first direction, as well as in a second direction. The first direction differs from the second direction. The inspection system further includes a detector arranged within the path of the emanating light so that the second portion of the emanating light that is transmitted by the PSF impinges on the detector to thereby form an image of at least a portion of the sample and an analyzer for receiving the image and determining whether there are any defects present on the sample portion by analyzing the received image.

In one implementation, the first direction is perpendicular to the second direction. In a further aspect, the sub-regions are arranged to facilitate inhibition of portions of the emanating light at a particular angle resulting from patterns on the sample. For example, the angle is 45 or 90 degrees from a plane of incidence. In a specific implementation, the PSF has a pair of plates formed from a material that substantially transmits ultraviolet light and are sized to cover an aperture of the emanating light, the plates being arranged parallel to each other, a first indium tin oxide (ITO) layer deposed on a first one of the plates, and a second ITO layer deposed on a second one of the plates. The first and second ITO layer are positioned between the plates. The first and/or the second ITO layer is divided into portions along both the first and second directions. The liquid crystal layer is arranged between the first ITO layer and the second ITO layer portions.

In a further embodiment, the first ITO layer is divided into portions and the second layer is not. The system further includes a controller configured for selectively apply a voltage potential difference between at least a one of the first ITO layer portions and the second ITO layer so that an adjacent portion of the liquid crystal layer allows transmission of a first portion of the emanating light while another portions of the liquid crystal layer on which a voltage potential difference is not applied inhibits a second portion of the emanating light through the PSF. In one aspect, the voltage potential difference is greater than a predetermined threshold, and the adjacent portion of the liquid crystal layer allows transmission when a voltage potential difference is applied that is greater than the predetermined threshold. In an alternative embodiment, the voltage potential difference is less than a predetermined threshold, and the adjacent portion of the liquid crystal layer allows transmission when a voltage potential difference is applied that is less than the predetermined threshold.

In a specific embodiment, the first ITO layer is divided into a plurality of portions that are arranged in a plurality of rows and the second ITO layer is divided into a plurality of columns. The system includes a controller configured to apply a first voltage potential difference between a selected row and a selected column so that a portion of the liquid crystal layer that is adjacent to an intersection of the selected row and column changes from being configured to inhibit to being configured to allow a corresponding portion of the emanating light. In a further aspect, the controller is further configured to apply a second voltage potential difference between the selected row and the selected column that previously had a first voltage applied there between so that the portion of the liquid crystal layer that is adjacent to the intersection of the selected row and column remains configured to allow the corresponding portion of the emanating light. The second potential difference is lower than the first potential difference. In yet a further aspect, the controller is further configured to apply a third voltage potential difference between the selected row and the selected column that previously had a second voltage applied there between so that the portion of the liquid crystal layer that is adjacent to the intersection of the selected row and column changes from being configured to allow to being configured to inhibit the corresponding portion of the emanating light. The third potential difference is lower than the second potential difference. In a further implementation, the controller is further configured to apply a fourth voltage potential difference between the selected row and the selected column that previously had a third voltage applied there between so that the portion of the liquid crystal layer that is adjacent to the intersection of the selected row and column remains configured to inhibit the corresponding portion of the emanating light. The fourth potential difference is higher than the third potential difference. In a preferred embodiment, the liquid crystal layer is a bi-stable material.

In another embodiment, the invention pertains to a method of detecting anomalies on a sample. An incident light beam is directed onto a sample. A first spatial portion of a emanating light beam, which results from the incident light beam hitting the sample, is selectively transmitted to a detector positioned within an image plane of such emanating light beam. The first spatial portion is transmitted by applying a first voltage potential difference between a first row and a first column of a programmable spatial filter (PSF) having a plurality of addressable rows and columns. A second spatial portion of the emanating light beam is inhibited through the PSF to the detector.

In a further aspect, the transmission of the first spatial portion of the emanating light is maintained by applying a second voltage potential difference between the first row and the first column. The second voltage potential difference is lower than the first voltage potential difference. In a further aspect, the first spatial portion of the emanating light is inhibited through the PSF from reaching the detector by applying a third voltage potential difference to the first row and the first column. The third voltage potential difference is lower than the second voltage potential difference. In another aspect, the inhibition of the first spatial portion of the emanating light is maintained by applying the second voltage potential difference between the first row and the first column. In yet another embodiment, the second spatial portion of the emanating light beam is inhibited from reaching the PSF the detector is accomplished by applying a second voltage potential to a second row and a second column, where the second voltage being lower than the first voltage.

These and other features and advantages of the present invention will be presented in more detail in the following specification of the invention and the accompanying figures which illustrate by way of example the principles of the invention.

DETAILED DESCRIPTION OF SPECIFIC EMBODIMENTS

Reference will now be made in detail to a specific embodiment of the invention. An example of this embodiment is illustrated in the accompanying drawings. While the invention will be described in conjunction with this specific embodiment, it will be understood that it is not intended to limit the invention to one embodiment. On the contrary, it is intended to cover alternatives, modifications, and equivalents as may be included within the spirit and scope of the invention as defined by the appended claims. In the following description, numerous specific details are set forth in order to provide a thorough understanding of the present invention. The present invention may be practiced without some or all of these specific details. In other instances, well known process operations have not been described in detail in order not to unnecessarily obscure the present invention.

Figure 1:
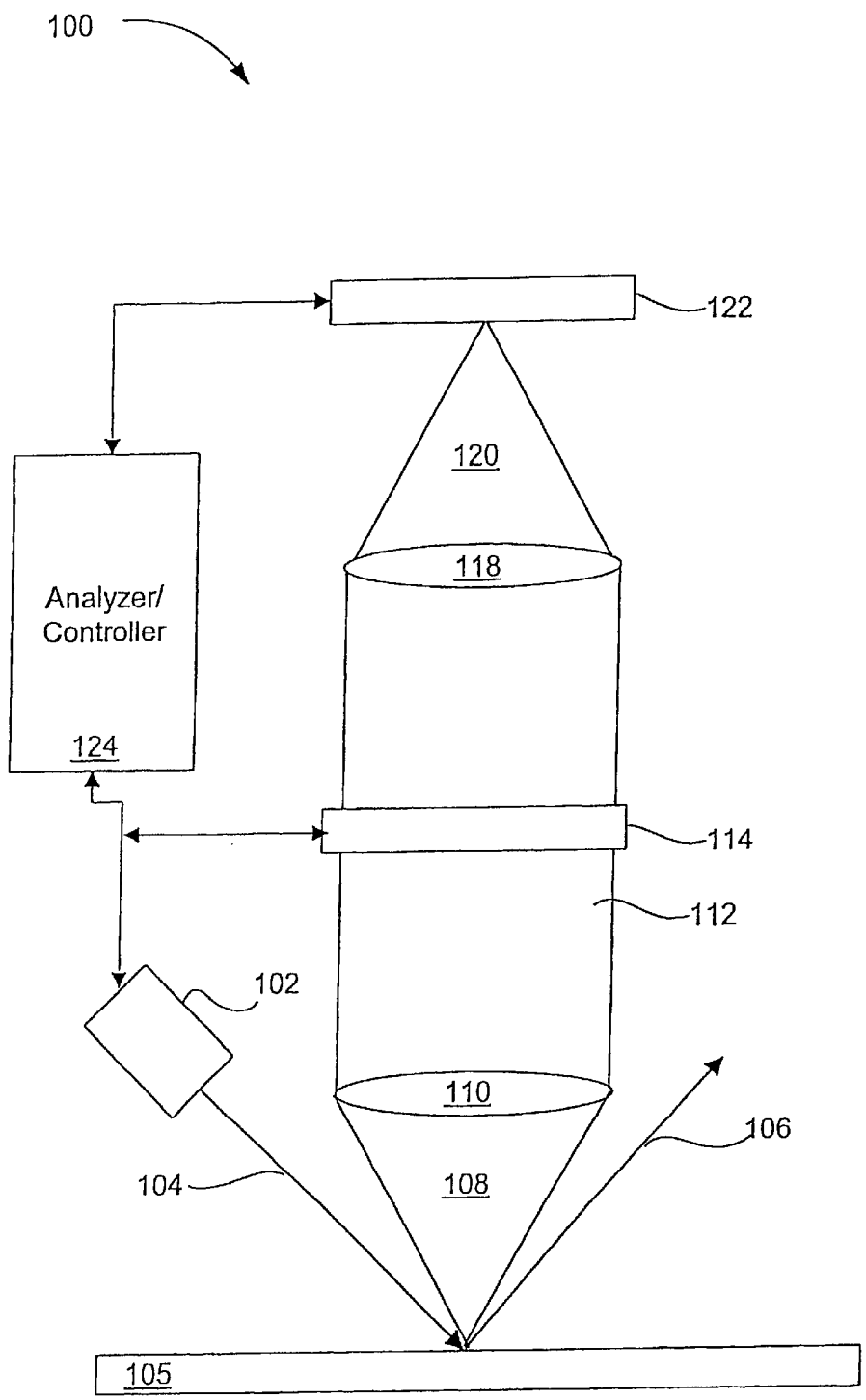
FIG. 1 is a simplified diagrammatic illustration of a darkfield optical inspection system in accordance with one embodiment of the present invention.

FIG. 1 is a simplified diagrammatic illustration of a darkfield optical inspection system 100 in accordance with one embodiment of the present invention. The illustrated inspection system 100 of FIG. 1 only includes features that will facilitate discussion of the embodiments of the present invention. FIG. 1 does not include several typical components of an inspection system so as to not obscure the present invention. Additionally, the relative dimensions of the components and placement of such components of FIG. 1 may be distorted so as to better illustrate embodiments of the present invention. As shown, the inspection system 100 includes a light source 102 for generating and directing a light or electromagnetic beam 104 onto a surface of sample 105.

The sample may be any suitable device or structure that may be inspected for defects using optical inspection techniques. By way of examples, the sample may include wafers, reticles, photo masks, flat panels and other specimens. The defects may include any suitable defect that is detectable through optical inspection techniques. Defects that tend to scatter light are detectable through darkfield techniques include, but are not limited to, particles on the sample and voids within the sample surface.

A portion of the incident beam is reflected off the sample 105 as reflected beam 106. Additionally, portions of the beam are scattered off the sample 105 as scattered light 108. Various characteristics of the sample may result in portions of the incident beam 104 being scattered as scattered light 108. Particular types of defects (e.g., particles or voids on the sample surface) may cause the incident beam to scatter. Repeating patterns on the sample that are not defects may also cause the incident beam to scatter. For example, typical integrated circuit repetitive designs may causes the incident light to scatter.

The scattered light 108 is directed through a first lens 110 that outputs collimated scattered light 112. Any suitable mechanism may be utilized to collect the scattered light, besides the first lens 110. For example, a pair of side mirrors may be used to direct the scattered light 108 towards a programmable spatial filter (PSF) 114. As shown, the first lens 110 collects the scattered light 108 and directs it towards PSF 114 which is positioned within the Fourier transform plane. Although the PSF is described herein as filtering "scattered" light, of course, the PSF may filter any type of light, such as reflected light.

In general terms, the PSF 114 is configurable to effectively inhibit one or more portions of the scattered light and effectively transmit portions of the scattered light for a light source within the UV wavelength range. Preferably, the PSF has a minimum extinction value of about 400:1 and a minimum transmission value of about 40 percent for an incident light beam having a wavelength between about 340 nm and about 400 nm. Most preferably, the PSF has a minimum extinction value of about 500:1 and a minimum transmission value of about 50 percent. The portions of the scattered light that are inhibited are substantially prevented from reaching the second lens 118, while scattered light that is transmitted substantially reaches the second lens 118.

Any suitable optical inspection system may be modified to incorporate one or more of the programmable spatial filter embodiments of the present invention. For example, the spatial filtered inspection mechanisms of the present invention may be combined with any other suitable optical inspection system. In a specific implementation, an inspection tool may include darkfield inspection capabilities and brightfield inspection capabilities. Several embodiments of a combination darkfield and brightfield system are described in U.S. Pat. No. 5,822,055 by Tsai et al., issued Oct. 13, 1998 and U.S. Pat. No. 6,201,601 by Vaez-Iravani et al., issued Mar. 13, 2001, which patents are commonly assigned and herein incorporated by reference in their entirety. These inspection systems may be easily modified to include a spatial filter of the present invention.

Referring back to FIG. 1, the second lens is configured to direct the transmitted scattered light 120 towards detector 122 positioned within the image plane. The detector is configured to generate an image of at least a portion of a sample that corresponds to the scattered light. The resulting image may then be received into an analyzer 124, where the analyzer 124 determines whether there are any defects present on the sample portion by analyzing the received image. The analyzer or controller 124 may be configured to perform any suitable techniques of the present invention, as well as typical control or monitoring mechanisms of the inspection system 100. By way of examples, the analyzer or controller 124 may be configured to configure various components of the inspection system, such as the detector 122, the PSF 114, and the light source 102, or to monitor characteristics of various components.

Figure 2A:
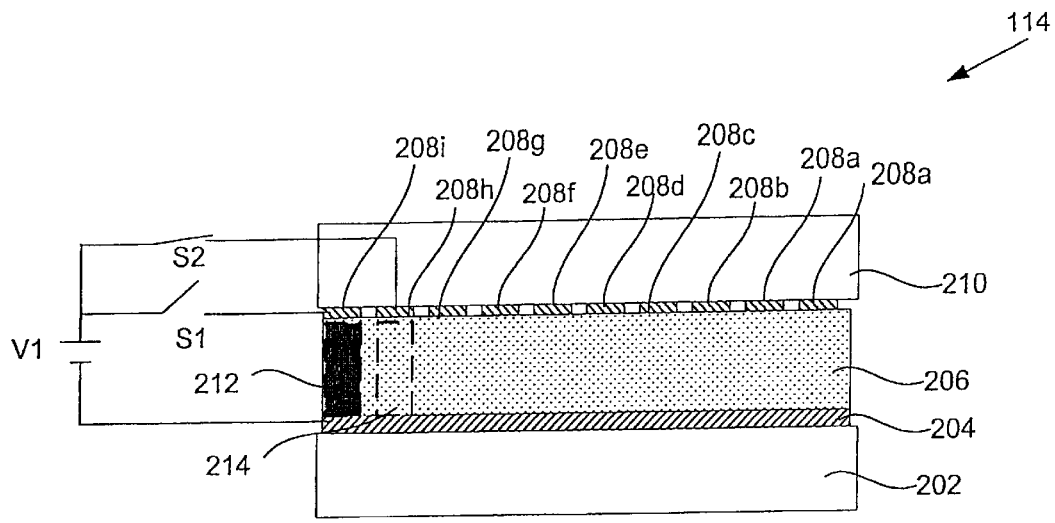
FIGS. 2A and 2B illustrate a side view and a top view, respectively, of the programmable spatial filter of FIG. 1 in accordance with one embodiment of the present invention.
Figure 2B:
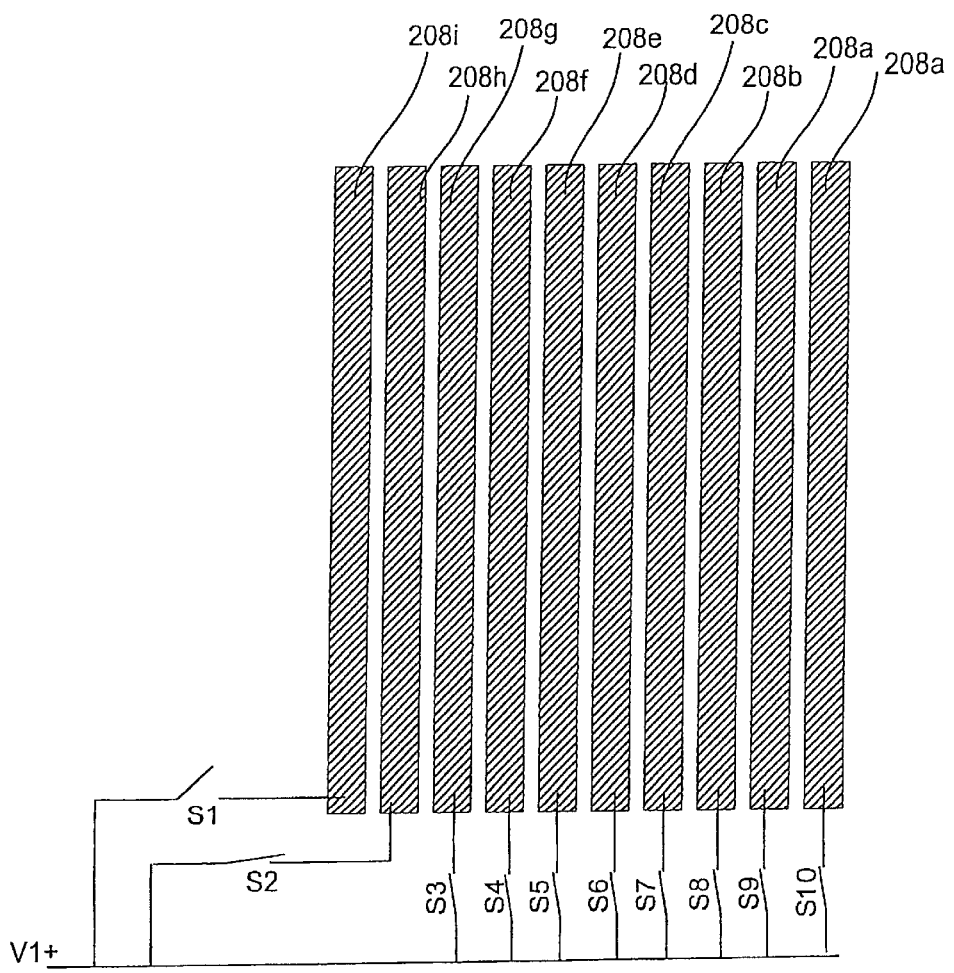

The PSF may be constructed in any suitable manner so as to achieve effective extinction and transmission performance under UV light conditions (e.g., the above described extinction and transmission values). FIGS. 2A and 2B illustrate a side view and a top view, respectively, of the programmable spatial filter 114 of FIG. 1 in accordance with one embodiment of the present invention. In one implementation, the PSF is sized to cover the aperture of the scattered light. As shown, the PSF includes a pair of plates 202 and 210. The plates are formed from a material that substantially transmits ultraviolet light, i.e., the plates are each UV compatible. In one implementation, the plates are formed from UV grade glass. In the illustrated embodiment, the plates are arranged parallel to each other and sized to cover an aperture of the scattered light.

The PSF 114 also includes a first indium tin oxide (ITO) layer 204 and a second ITO layer 208 formed from a plurality of ITO layer portions 208a through 208i deposed on a first one of the plates 202 and a second one of the plates 210, respectively. The ITO layers are conductive and transmit UV light effectively. Of course, any suitable material may be used, instead of ITO, that is both conductive and transparent. The first and second ITO layers 204 and 208 are deposed on each of the plates 202 and 210, respectively. An ITO layer or pattern may be more easily deposited onto the plate if the plate is formed from glass, as compared to when the plate is formed from a conventional plastic. In one embodiment shown in FIG. 2B, the second ITO layer portions 208 form a plurality of parallel strips 208a through 208i. In one embodiment, the ITO layers are relatively thin so as to allow acceptable performance under UV conditions. A thickness that results in a sheet resistance between about 100 and about 300 Ω per square has acceptable conductance and transmission capabilities for UV light.

The PSF also includes a material 206 between the first and second ITO layers that is selectively configurable to provide UV compatible transmission and opacity performance. For example, a polymer stabilized liquid crystal material may be used. Such a liquid crystal material may be obtained from any suitable company that specializes in liquid crystal applications, such as AlphaMicron or Kent Optronics, both of Kent, Ohio. Polymer stabilized liquid crystal materials are described further in the article "Assemble-Averaged Dynamic Light Scattering from Polymer-Stabilized Liquid Crystals." by P. Y. Lui, L. C. Chien, Mol. Crys. Liq. Cyrs. 348, 187–205 (2000) and U.S. Pat. No. 5,691,795 by Doane et al., issued Nov. 25, 1997, which article and patent are incorporated herein by reference in their entirety.

Each of the second ITO layer portions 208 are coupled to a mechanism for selectively applying a voltage potential difference between one or more of the second ITO layer portions 208 and the first ITO layer 204. As shown in FIG. 2B, ITO layer portion 208a is coupled to switch S10, while ITO layer portion 208i is coupled to switch S1. Each of the switches S1 through S10 are coupled to voltage source V1. The voltage source V1 is also coupled to the first ITO layer 204. Thus, the voltage V1 may be applied selectively between one or more second ITO layer portions 208 and the first ITO layer 204. The voltage may be applied selectively (or selectively not applied) to one or more of the second ITO layer portions 208 by any suitable mechanism. In the illustrated embodiment, the controller 124 of FIG. 1 is configured to control the switches S1 through S10 of FIG. 2B.

When substantially no voltage potential difference is applied between one of the second ITO portions 208 and the first ITO layer 204 (or when the voltage difference drops below a predetermined threshold), the portion of the liquid crystal material 206 that is positioned between the selected second ITO portion 208 and the first ITO layer 204 generally becomes opaque to the scattered light going through such liquid crystal portion. In an alternative implementation, a voltage difference above a predetermined threshold may cause the liquid crystal material to become opaque. This opacity causes a corresponding spatial portion of the scattered light to be inhibited from reaching the detector. The opaque portion of the liquid crystal causes a substantial portion of the scattered light directed through the "deactivated" second ITO portion (e.g., 208i) to be scattered away from the detector. As shown in FIG. 2A, S1 is open so that a voltage potential difference is not applied between second layer portion 208i and the first layer 204 to thereby cause a portion 212 of the liquid crystal 206 to become opaque. In contrast, S2 is closed so that a voltage potential difference is applied between the second layer portion 208h and the first layer 204 to thereby cause a portion 214 to become clear. Any number of the second ITO layer portions 208 may be selectively switched to not be decoupled from voltage V1 so that corresponding portions of liquid crystal 206 may become opaque and inhibit different spatial portions of the scattered light from the sample.

In one embodiment, the ITO layer portions 208 are selectively deactivated to inhibit certain spatial scattered light portions that result from repeating patterns on the sample, rather than defects. That is, the ITO layers are selected to correspond to portions of the scattered light that contain "nuisance" defects. These inhibited portions of the scattered light may include sharp, bright diffraction spots resulting from repeating patterns on the sample Alternatively, the inhibited spatial portions may include scattered light at particular angles with respect to the plane of incidence, such as 45 and 90 degrees, that result from repeating lines on the sample. A selection example is described further below with reference to FIG. 6.

Figure 3:
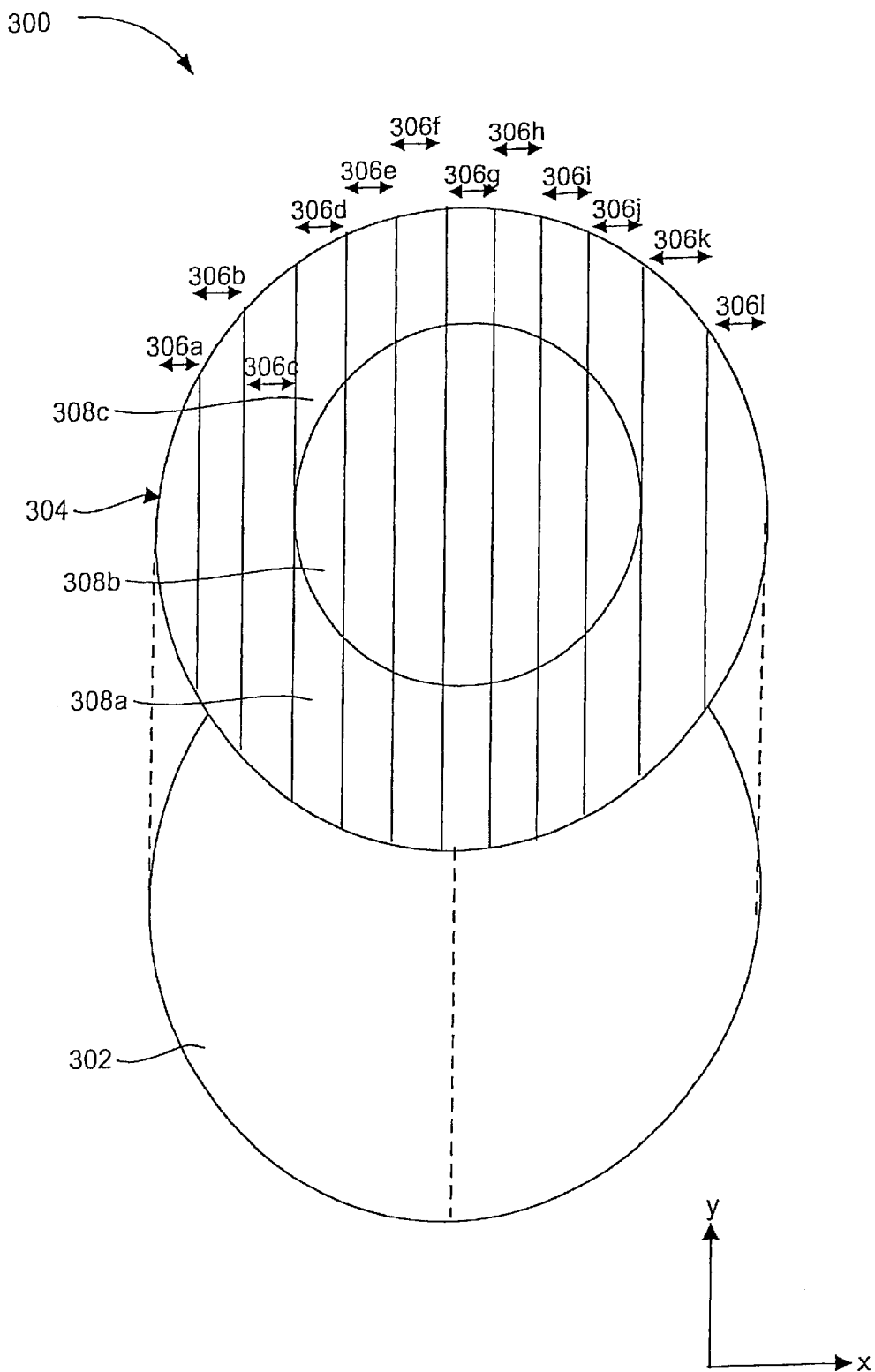
FIG. 3 is a illustration of a segmented ITO layer of a programmable spatial filter in accordance with an alternative embodiment of the present invention.

FIG. 3 is a illustration of a first segmented ITO layer 304 and a second ITO layer 302 of a PSF in accordance with an alternative embodiment of the present invention. These ITO layers may be used to form part of a programmable spatial filter, such as the PSF illustrated in FIG. 2A. That is, the ITO layers 304 and 302 of FIG. 3 may replace the ITO layers 204 and 208 of FIG. 2A. All the additional features described above in relation to FIGS. 2A and 2B may be used within a PSF which includes the ITO layers of FIG. 3. Referring back to FIG. 3, the first ITO layer 304 is formed from a plurality of strips 306a through 306l. At least a portion of the strips 306 are "segmented." As shown, strip 306d includes segments 308a through 308c. Likewise, strips 306e through 306j are each also segmented. Each strip or segment may be individually deactivated. For instance, a voltage difference may be decoupled from between segment 308a and the second ITO layer 302. Likewise, a voltage difference may be decoupled from between segment 308b and the second ITO layer 302. A voltage difference may also be decoupled from between any of the strips that are not segmented. For instance, a voltage difference may be decoupled from between strip 306a and the second ITO layer 302.

Segmentation of one of the ITO layers allows greater flexibility in inhibiting different spatial portions of the scattered light. In other words, the PSF can be configured to inhibit selected spatial portions of the scattered light in two directions (e.g., x and y). The PSF embodiments of FIGS. 2A and 2B merely selectively inhibit spatial portions of the scattered light in one direction. That is, one may selectively inhibit one or more strips of scattered light in a single dimension or direction. In contrast, the embodiment of FIG. 3 allows one to selectively inhibit different portions of scattered light in an x direction by selecting one or more of the strips (i.e., 306a through 306l) and in a y direction by selecting one or more of the segments (e.g., 308a, 308b, and/or 308c). The segments of the ITO layer may be arranged in any two suitable directions, which do not have to be perpendicular to each other as shown in the illustrated embodiment.

Figure 4A:
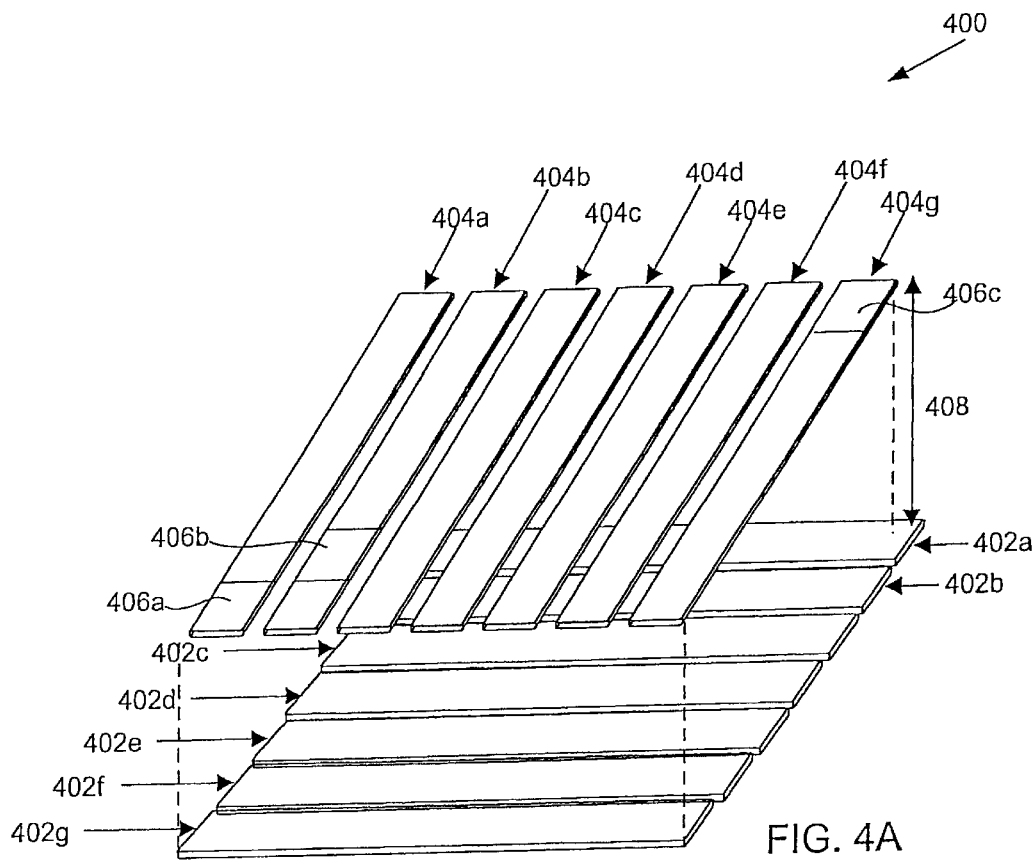
FIGS. 4A and 4B illustrate a perspective view and a top view, respectively, of a first and second ITO layer of a programmable spatial filter in accordance with a two dimensional embodiment of the present invention.
Figure 4B:
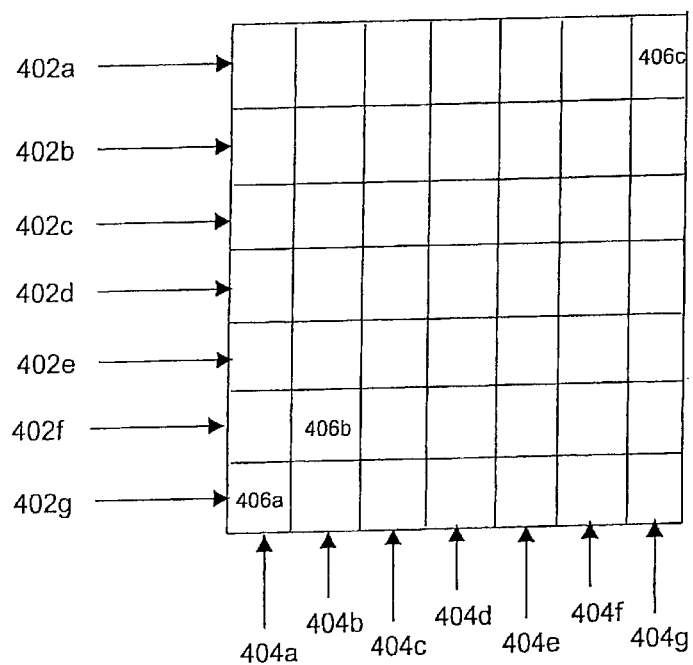

FIGS. 4A and 4B illustrate a perspective view and a top view, respectively, of a first and second ITO layer of a programmable spatial filter in accordance with a two dimensional embodiment of the present invention. In this embodiment, a two dimensional array of ITO portions may be selectively deactivated so that a corresponding two dimensional array of liquid crystal portions are selectively turned opaque. The ITO layers of FIGS. 4A and 4B may be incorporated into the PSF of FIGS. 2A and 2B. That is, the ITO layers of FIGS. 4A and 4B may be substituted for the ITO layers of FIGS. 2A and 2B. All the additional features described above in relation to FIGS. 2A and 2B may be used within a PSF which includes the ITO layers of FIGS. 4A and 4B.

As shown, a first ITO layer 404 is formed into a plurality of strips or "columns." A second ITO layer 402 is formed into a plurality of strips or "rows." The first ITO layer 404 is positioned over the second ITO layer 402. A liquid crystal material 408 is positioned between the first ITO layer 404 and the second ITO layer 402. The first and second ITO layers form a plurality of intersections 406. Each intersection 406 corresponds to a portion of the liquid crystal material 408 that is positioned between the intersection area 406. Of course, the two ITO layers may be arranged in any suitable number and type of shapes so as to form a plurality of intersections between pairs of adjacent first and second ITO layer portions.

Referring to FIG. 4B, each intersection may be deactivated by decoupling or reducing a voltage from a selected row of ITO layer 402 and a selected column of ITO layer 404. For example, when a particular voltage difference that is less than or equal to a predetermined threshold is applied between the lower layer row 402g and the upper column 404a, intersection 406a is deactivated. That is, the liquid crystal material that is below the intersection 406a or between the overlapping column 404a and row 402g becomes opaque. By way of another example, when a voltage potential difference below the predetermined level is applied between row 402a and column 404g, the intersection 406c becomes deactivated so that the liquid crystal material below this intersection 406c becomes opaque. In an alternative embodiment, an intersection becomes opaque when a voltage difference applied between the overlapping column and row rises above a predetermined threshold.

Figure 5:
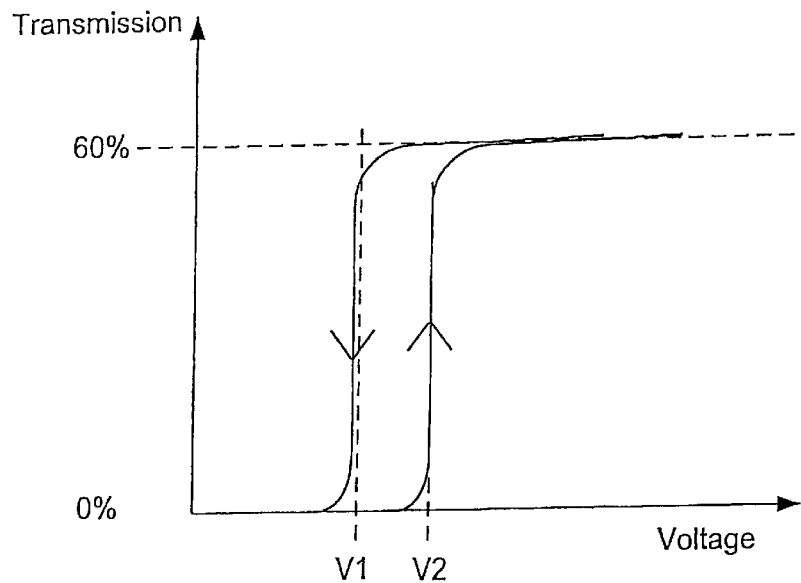
FIG. 5 is a graph of transmission as a function of the voltage applied between any of the intersections of the ITO layer of FIGS. 4A and 4B in accordance with one embodiment of the present invention.

Preferably, the liquid crystal material is formed from a bi-stable material. FIG. 5 is a graph of transmission as a function of the voltage applied between any of the intersections of the ITO layer of FIGS. 4A and 4B in accordance with one embodiment of the present invention. At zero voltage potential difference, there is zero transmission through the ITO intersection. When the voltage difference is greater than V2, the transmission percentage through such intersection increases to a plateau, for example, of 60%. The intersection stays at 60% transmission until the voltage difference falls below V1. That is, the voltage difference may fall below the voltage V2 that activated such intersection and still remain "on".

Thus, the voltage to turn on a particular intersection may be met by a contribution of voltages applied to both a particular row and a particular column. In one implementation, the voltage of either the corresponding row or column may be removed without causing the particular intersection to switch to the off state. In other words, the intersection is maintained in an on state for a range of voltages (i.e., V1 through V2) below the initial "turn-on" voltage V2. For example, 50 volts may be applied to a first row and 50 volts may be applied to a first column to activate a particular intersection. The first row voltage may be then decreased to zero, while the first column remains at 50 volts. If V1 corresponds to 50 volts and V2 corresponds to a 100 volts, the intersection will remain on even though it is now at 50 volts, instead of 100 volts. This bimodal scheme allows another intersection in the same row or column as a particular intersection to deactivate without turning off the particular intersection.

When the intersection voltage falls below V1, the intersection switches to the off state and the corresponding liquid crystal portion becomes opaque and inhibits a previously transmitted portion of the scattered light to now be blocked from passing through the PSF. For example, the above described particular intersection may be turned off by having both voltages of the first row and first column fall below V1 or 50 volts (e.g., the first row and column fall to 0 V). A particular intersection will remain off when the voltage at such intersection is increased to voltages between V1 and V2. Even if the voltage of a particular row or column goes above V1 or 50 volts, the particular intersection remains off. This bimodal scheme allows another intersection in the same row or column as a particular intersection to activate without turning on the particular deactivated intersection.

Figure 6:
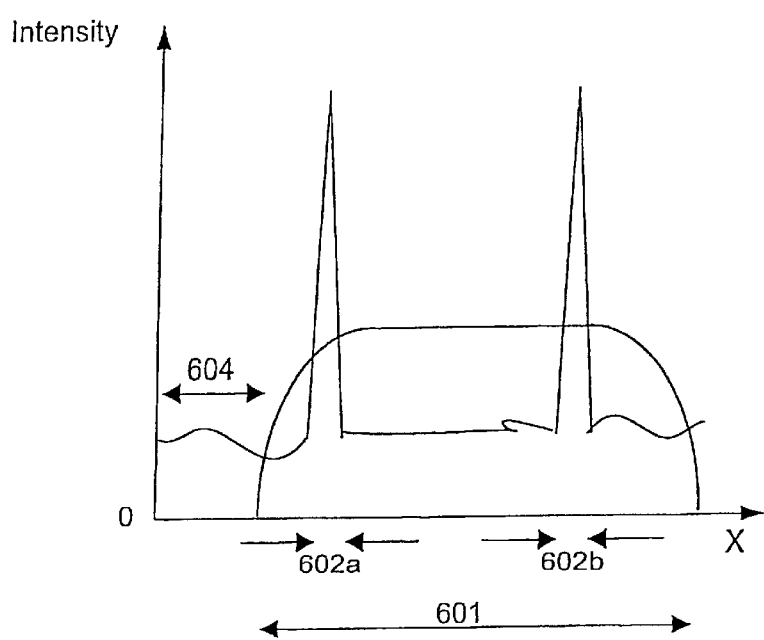
FIG. 6 illustrates an example of scattered light from a sample as a function of the x direction.

The PSF embodiments of the present invention may be used to selectively mask various portions of the scattered light that correspond to "nuisance defects", as well as portions of the scattered light that are known to not contain the "real defect." FIG. 6 illustrates an example of scattered light intensity from a sample as a function of the x direction. As shown, portion 601 of the scattered light corresponds to the defect itself. The scattered light portions 602a and 602b correspond to "nuisance defects" in the form of bright, sharp diffraction spots resulting from a repeating pattern on the sample. The scattered light portion 604 corresponds to a portion of the scattered light that is known to not contain a defect. The PSF of the present invention may be used to inhibit scattered light from portions 602a, 602b, and 604 so as to isolate and enhance the actual defect 601.

Although the foregoing invention has been described in some detail for purposes of clarity of understanding, it will be apparent that certain changes and modifications may be practiced within the scope of the appended claims. Therefore, the described embodiments should be taken as illustrative and not restrictive, and the invention should not be limited to the details given herein but should be defined by the following claims and their full scope of equivalents.

What is claimed is:

1. An optical inspection system for detecting anomalies on a sample, comprising:

a light source for directing an incident light beam having a wavelength between about 340 nanometers and 400 nanometers onto a sample;

a programmable spatial filter (PSF) arranged in a path of light emanating from the sample in response to the incident light beam, wherein the PSF is configurable to inhibit or transmit one or more selected portions of the emanating light, wherein the selected portions of the emanating light may be selected from a plurality of emanating light portions arranged along a first direction, as well as in a second direction, the first direction differing from the second direction, wherein the PSF is formed from UV compatible materials so as to substantially transmit or inhibit UV light;

a detector arranged within the path of the emanating light so that the second portion of the emanating light that is transmitted by the PSF impinges on the detector to thereby form an image of at least a portion of the sample; and an analyzer for receiving the image and determining whether there are any defects present on the sample portion by analyzing the received image.

2. A system as recited in claim 1, wherein the first direction is perpendicular to the second direction.

3. A system as recited in claim 1, wherein the sub-regions are arranged to facilitate inhibition of portions of the emanating light at a particular angle resulting from patterns on the sample.

4. A system as recited in claim 1, wherein the angle is 45 degrees from a plane of incidence.

5. A system as recited in claim 1, wherein the angle is 90 degrees from a plane of incidence.

6. A system as recited in claim 1, wherein the PSF comprises:

a pair of plates formed from a material that substantially transmits ultraviolet light and are sized to cover an aperture of the emanating light, the plates being arranged parallel to each other;

a first indium tin oxide (ITO) layer deposed on a fit one of the plates;

a second ITO layer deposed on a second one of the plates, wherein the first and second ITO layer are positioned between the plates, wherein the first and/or the second ITO layer is divided into portions along both the first and second directions; and a liquid crystal layer arranged between the first ITO layer and the second ITO layer portions.

7. A system as recited in claim 6, wherein the first ITO layer is divided into portions and the second layer is not, the system further comprising a controller configured for selectively applying a voltage potential difference between at least a one of the first ITO layer portions and the second ITO layer so that an adjacent portion of the liquid crystal layer allows transmission of a first portion of the emanating light while another portions of the liquid crystal layer on which a voltage potential difference is not applied inhibits a second portion of the emanating light through the PSF.

8. A system as recited in claim 7, wherein the voltage potential difference is greater than a predetermined threshold, and wherein the adjacent portion of the liquid crystal layer allow transmission when a voltage potential difference is applied that is greater than the predetermined threshold.

9. A system as recited in claim 7, wherein the voltage potential difference is less than a predetermined threshold, and wherein the adjacent portion of the liquid crystal layer allow transmission when a voltage potential difference is applied that is less than the predetermined threshold.

10. A system as recited in claim 6, wherein the first ITO layer is divided into a plurality of portions that are arranged in a plurality of rows and the second ITO layer is divided into a plurality of columns, the system comprising a controller configured to apply a first voltage potential difference between a selected row and a selected column so that a portion of the liquid crystal layer that is adjacent to an intersection of the selected row and column changes from being configured to inhibit to being configured to allow a corresponding portion of the emanating light.

11. A system as recited in claim 10, wherein the controller is further configured to apply a second voltage potential difference between the selected row and the selected column that previously had a first voltage applied there between so that the portion of the liquid crystal layer that is adjacent to the intersection of the selected row and column remains configured to allow the corresponding portion of the emanating light, wherein the second potential difference is lower than the fist potential difference.

12. A system as recited in claim 11, wherein the controller is further configured to apply a third voltage potential difference between the selected row and the selected column that previously had a second voltage applied there between so that the portion of the liquid crystal layer that is adjacent to the intersection of the selected row and column changes from being configured to allow to being configured to inhibit the corresponding portion of the emanating light wherein the third potential difference is lower than the second potential difference.

13. A system as recited in claim 12, wherein the controller is further configured to apply a fourth voltage potential difference between the selected row and the selected column that previously had a third voltage applied there between so that the portion of the liquid crystal layer that is adjacent to the intersection of the selected row and column remains configured to inhibit the corresponding portion of the emanating light wherein the fourth potential difference is higher than the third potential difference.

14. A system as recited in claim 13, wherein the liquid crystal layer is a bi-stable material.

15. An optical inspection system for detecting anomalies on a sample, comprising:
 a light source for directing an incident light beam having a wavelength between about 340 nanometers and 400 nanometers onto a sample;
 a programmable spatial filter (PSF arranged in a path of light emanating from the sample in response to the incident light beam, wherein the PSF comprises:
  a pair of plates formed from a material that substantially transmits ultraviolet light and are sized to cover an aperture of the emanating light, the plates being arranged parallel to each other;
  a first indium tin oxide (ITO) layer deposed on a first one of the plates, the first ITO layer being divided into a plurality of first portions along a first direction;
  a second ITO layer deposed on a second one of the plates, wherein the first and second ITO layer are positioned between the plates, the first ITO layer being divided into a plurality of fit portions along a second direction that differs from the fist direction;
  liquid crystal layer arranged between the first ITO layer and second ITO layer portions, the liquid crystal layer being formed from a bi-stable material; and
  a controller configured for selectively applying a voltage potential difference between at least a pair of first and second ITO layer portions so that an adjacent portion of the liquid crystal layer are configured to inhibit or transmit one or more first portions of the emanating light;
 a detector arranged within the path of the emanating light so that the portions of the emanating light that are transmitted by the PSF impinge on the detector to thereby form an image of at least a portion of the sample; and
 an analyzer for receiving the image and determining whether there are any defects present on the sample portion by analyzing the received image.

16. A system as recited in claim 15, wherein the liquid crystal is a UV compatible material.

17. A system as recited in claim 16, wherein the liquid crystal is a polymer stabilized liquid crystal material.

18. A system as recited in claim 17, wherein the pair of plates are formed from a UV grade glass.

19. A system as recited in claim 18, wherein the first and second ITO layers have a thickness value so as to result in between about 100 and about 300 $\Omega$ per square.

20. A system as recited in claim 15, wherein the voltage potential difference is greater than a predetermined threshold, and wherein the adjacent portion of the liquid crystal layer allow transmission when a voltage potential difference is applied that is greater than the predetermined threshold.

21. A system as recited in claim 15, wherein the voltage potential difference is less than a predetermined threshold, and wherein the adjacent portion of the liquid crystal layer allow transmission when a voltage potential difference is applied that is less than the predetermined threshold.

22. A method of detecting anomalies on a sample, the method comprising:
 directing an incident light beam having a wavelength between about 340 nanometers and 400 nanometers onto a sample;
 selectively transmitting a first spatial portion of a emanating light beam through a programmable spatial filter (PSF), which results from the incident light beam hitting the sample, to a detector positioned within an image plane of such emanating light beam so that the first spatial portion has a minimum transmission value of about 40 percent wherein the first spatial portion is transmitted by applying a first voltage potential difference between a first row and a first column of the programmable spatial filter (PSF) having a plurality of addressable rows and columns; and
 inhibiting a second spatial portion of the emanating light beam through the PSF to the detector so that the second spatial portion(s) have a minimum extinction value of about 400:1.

23. A method as recited in claim 22, further comprising maintaining the transmission of the first spatial portion of the emanating light by applying a second voltage potential difference between the first row and the first column, the second voltage potential difference being lower than the first voltage potential difference.

24. A method as recited in claim 23, further comprising inhibiting the first spatial portion of the emanating light through the PSF from reaching the detector by applying a third voltage potential difference to the first row and the first column, wherein the third voltage potential difference is lower than the second voltage potential difference.

25. A method as recited in claim 24, further comprising maintaining the inhibition of the first spatial portion of the emanating light by applying the second voltage potential difference between the first row and the first column.

26. A method as recited in claim 22, wherein inhibiting the second spatial portion of the emanating light beam from reaching the PSF the detector is accomplished by applying a second voltage potential to a second row and a second column, the second voltage being lower than the first voltage.

27. A method as recited in claim 26, wherein the second voltage is less than the first voltage by a predetermined amount when the second spatial portion of the emanating light was previously being inhibited from passing through the PSF.

28. A method as recited in claim 26, wherein the second voltage is less than the first voltage by a second predetermined amount that is greater than the first predetermined amount when the second spatial portion of the emanating light was previously being transmitted through the PSF.

29. A method as recited in claim 22, further comprising detecting and analyzing the emanating light beam to thereby detect defects on the sample.

30. A system as recited in claim 1, where wherein when a voltage potential difference is applied to or removed from the materials of the PSF, the materials have either an opaque property to thereby inhibit at least a first portion of the emanating light with a minimum extinction value of about 400:1 or have a transparency property to thereby transit at least at least a second portion of the emanating light with a minimum transmission value of about 40 percent for the incident light beam.

* * * * *

UNITED STATES PATENT AND TRADEMARK OFFICE
CERTIFICATE OF CORRECTION

PATENT NO. : 6,686,995 B2
DATED : February 3, 2004
INVENTOR(S) : Wilk et al.

It is certified that error appears in the above-identified patent and that said Letters Patent is hereby corrected as shown below:

Column 10,
Line 51, change "fit" to -- first --.

Column 11,
Line 31, change "fist" to -- first --.

Column 12,
Line 4, change "fit" to -- fist --.
Line 5, change "fist" to -- first --.
Line 6, before "liquid;" add an -- a --.

Column 14,
Line 15, change "transit" to -- transmit --.

Signed and Sealed this

Twenty-seventh Day of July, 2004

JON W. DUDAS
*Acting Director of the United States Patent and Trademark Office*